US010631846B2

(12) United States Patent
Gadlage et al.

(10) Patent No.: US 10,631,846 B2
(45) Date of Patent: Apr. 28, 2020

(54) SUTURE RETENTION MECHANISM

(71) Applicant: Cook Medical Technologies LLC, Bloomington, IN (US)

(72) Inventors: Kristyn Gadlage, Dyersburg, TN (US); Graham Barnett, Freedom, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 450 days.

(21) Appl. No.: 15/392,239

(22) Filed: Dec. 28, 2016

(65) Prior Publication Data

US 2017/0105717 A1  Apr. 20, 2017

Related U.S. Application Data

(62) Division of application No. 14/103,323, filed on Dec. 11, 2013, now Pat. No. 9,566,057.

(60) Provisional application No. 61/736,205, filed on Dec. 12, 2012.

(51) Int. Cl.
*A61B 17/04* (2006.01)
*A61B 17/00* (2006.01)

(52) U.S. Cl.
CPC ...... *A61B 17/0401* (2013.01); *A61B 17/0487* (2013.01); *A61B 2017/00818* (2013.01); *A61B 2017/0404* (2013.01); *A61B 2017/0414* (2013.01); *A61B 2017/0417* (2013.01); *A61B 2017/0451* (2013.01); *A61B 2017/0456* (2013.01); *A61B 2017/0458* (2013.01); *A61B 2017/0464* (2013.01)

(58) Field of Classification Search
CPC .... A61B 2017/0404; A61B 2017/0414; A61B 2017/0451; A61B 2017/0456; A61B 2017/0458; A61B 2017/0464; A61B 17/0401; A61B 17/0487
See application file for complete search history.

(56) References Cited

U.S. PATENT DOCUMENTS

| | | | | |
|---|---|---|---|---|
| 2,075,508 | A * | 3/1937 | Davidson | A61B 17/0401 24/712.9 |
| 4,291,698 | A * | 9/1981 | Fuchs | A61B 17/0487 24/132 AA |
| 6,018,851 | A * | 2/2000 | Anscher | F16G 11/101 24/115 G |
| 6,066,160 | A * | 5/2000 | Colvin | A61B 17/0487 606/151 |
| 6,582,443 | B2 * | 6/2003 | Cabak | A61B 17/0469 606/148 |
| 7,270,671 | B2 * | 9/2007 | Fuseri | A61B 17/0487 606/144 |

(Continued)

OTHER PUBLICATIONS

Spec. Sheet entitled T-PEX Anchor Set by OptiMed.

*Primary Examiner* — Julie A Szpira
(74) *Attorney, Agent, or Firm* — Brinks Gilson & Lione

(57) ABSTRACT

The present invention provides suture retention devices for retaining a suture on a bodily wall, e.g. for affixing the suture to the skin such as during the creation of an external percutaneous fluidic connection. In one embodiment, a device includes a base member and a swivel member. In another embodiment, the device includes a base member, first and second jaws, and a key. Operation of the swivel member or key serves to lock the suture to the device, and hence maintain tension on the suture while affixed to the skin.

20 Claims, 9 Drawing Sheets

(56) References Cited

U.S. PATENT DOCUMENTS

| | | | |
|---|---|---|---|
| 7,867,253 B2* | 1/2011 | McMichael | A61B 17/0487 606/232 |
| 7,875,056 B2* | 1/2011 | Jervis | A61B 17/0487 24/115 M |
| 8,540,740 B2 | 9/2013 | Lam et al. | |
| 8,945,181 B2 | 2/2015 | Taylor et al. | |
| 9,011,490 B2 | 4/2015 | Frankland et al. | |
| 9,107,655 B2* | 8/2015 | Stanley | A61B 17/0487 |
| 9,119,614 B2 | 9/2015 | Gadladge | |
| 10,098,628 B2* | 10/2018 | Fisher | A61B 17/0401 |
| 2005/0149120 A1* | 7/2005 | Collier | A61B 17/0401 606/232 |
| 2005/0149121 A1* | 7/2005 | Crombie | A61B 17/0483 606/232 |
| 2007/0021781 A1* | 1/2007 | Jervis | A61B 17/0487 606/232 |
| 2007/0276437 A1* | 11/2007 | Call | A61B 17/0487 606/232 |
| 2009/0062853 A1* | 3/2009 | McMichael | A61B 17/0487 606/232 |
| 2010/0057110 A1* | 3/2010 | Lampropoulos | A61B 17/0485 606/148 |
| 2011/0106155 A1* | 5/2011 | Theobald | A61B 17/0487 606/232 |
| 2013/0218206 A1* | 8/2013 | Gadlage | A61B 17/0487 606/232 |
| 2013/0238024 A1 | 9/2013 | Taylor et al. | |

\* cited by examiner

SUTURE RETENTION MECHANISM

CROSS-REFERENCE TO RELATED APPLICATIONS

This application is a divisional of U.S. application Ser. No. 14/103,323 filed on Dec. 11, 2013, and claims the benefit of U.S. Provisional Application Ser. No. 61/736,205 filed on Dec. 12, 2012, entitled "SUTURE RETENTION MECHANISM," the entire contents of which are incorporated herein by reference.

FIELD OF THE INVENTION

The present invention relates generally to external percutaneous connections to an internal organ or bodily lumen, and more particularly to a retention mechanism for sutures used in such external percutaneous connections.

BACKGROUND OF THE INVENTION

Many types of external percutaneous connections form to provide a patient or medical staff with access to an internal organ or bodily lumen. For example, semi-permanent connections are made through the skin for placement of IV lines, catheters, dialysis lines, colostomy bags in the like. Percutaneous endoscopic gastrostomy tubes, commonly known as PEG tubes, are used as a means of feeding when a person is unable to eat. PEG tubes are typically inserted through a small incision in the abdomen into the stomach. These tubes may be sutured in place, or large support bolsters having adhesive pad are used to anchor the tube in place such that a portion extends into the stomach, and an opposing portion extends out of the stomach and through the skin for external access. Sutures are often utilized to affix the stomach to the abdominal wall, e.g. prior to placing a gastric tube, in a procedure known as gastropexy. The suture or sutures are used to pull the stomach adjacent the abdominal wall, and then tied (sewn to the skin) to maintain the relative positioning while the tube is placed.

BRIEF SUMMARY OF THE INVENTION

The present invention provides suture retention devices for retaining a suture on a bodily wall, e.g. for affixing the suture to the skin such as during the creation of an external percutaneous fluidic connection. In one embodiment, a device includes a base member and a swivel member. The base member has an upper surface, a lower surface, and a bore extending from the upper surface to the lower surface. The bore defines a bore surface that includes a base jaw surface. The swivel member is rotatably attached to the base member for rotation between an open position and a closed position relative to the base member. The swivel member includes a swivel jaw surface in communication with the bore. The swivel jaw surface is engaged with the base jaw surface in the closed position such that a suture passing through the bore is fixed to the device. The swivel jaw surface is disengaged from the base jaw surface in the open position such that the suture is not fixed to the device.

According to further detailed aspects, the base member defines a recess in communication with the bore, the recess receiving the swivel member. The recess in the base member receives the swivel member in the closed position such that the base member and swivel member together have a disc shape. The recess preferably opens to the upper surface of the base member. The base member includes a side surface extending from the upper surface to the lower surface, and the recess may also open to the side surface.

According to still further detailed aspects, the device may also include a lock selectively fixing the swivel member to the base member. The lock may include a flexible tab formed on the swivel member and corresponding aperture formed in the base member. The swivel jaw surface and the base jaw surface each preferably include a series of teeth sized and structured to mesh in the closed position to fix the suture to the device. The swivel jaw surface moves towards the upper surface as the swivel jaw moves from the open position to the closed position. The swivel jaw surface selectively engages the base jaw surface as the swivel jaw approaches the closed position to draw the suture towards the upper surface.

In another embodiment, the device includes a base member, first and second jaws, and a key. The base member has an upper surface, a lower surface, and a bore extending from the upper surface to the lower surface. The base member also includes an internal recess in communication with the bore. The first jaw defines a first jaw surface and a second jaw defines a second jaw surface. The first and second jaws are positioned within the internal recess of the base member and are positioned to engage a suture passing through the bore. At least one of the jaws is slidably mounted within the recess and preferably is biased towards the other jaw. The key is selectively attachable to the base member, and the device includes an unlocked configuration where the key is attached to the base member and extends through the bore and into the recess between the first and second jaws to space the first and second jaw surfaces apart from one another. The device also includes a locked configuration where the key is detached from the base member and removed from the recess such that the first and second jaws surfaces engage the suture passing through the bore to fix the position of the suture relative to the base member.

According to further detailed aspects, the key includes a passageway extending therethrough that receives the suture. The key includes a key body and a locking tab projecting transversely to the key body, and the upper portion of the bore has an asymmetrical opening sized to permit passage of the key therethrough only when the key has a prescribed rotational position that aligns the locking tab relative to the asymmetrical opening. The key includes a handle sized larger than the asymmetrical opening such that the handle cannot pass through the upper portion of the bore.

According to still further detailed aspects, the first jaw is preferably biased by a spring positioned between the first jaw and a side surface of the base member. The base member may include a rod extending between opposing side surfaces of the base member, and the first jaw is the one jaw slidably mounted within the recess includes an aperture that slidably receives the rod. The second jaw may also be slidably mounted within the recess and includes an aperture that slidably receives the rod. Preferably, the base member includes a pair of spaced apart rods extending between opposing side surfaces of the base member, and the first and/or second jaw includes a pair of apertures that slidably receives the rods. The first and second jaw surfaces are preferably defined by first and second sets of elongated serrations sized and structured to mesh to define a tortuous engagement surface.

DETAILED DESCRIPTION OF THE INVENTION

The terms "proximal" and "distal" as used herein are intended to have a reference point relative to the user. Specifically, throughout the specification, the terms "distal" and "distally" shall denote a position, direction, or orientation that is generally away from the user and towards a target site, and the terms "proximal" and "proximally" shall denote a position, direction, or orientation that is generally towards the user and away from a target site. Thus, "proximal" and "distal" directions, portions of a device, or bodily regions, may depend on the point of entry for the procedure (e.g., percutaneously or laparoscopically or endoscopically).

Figure 1:
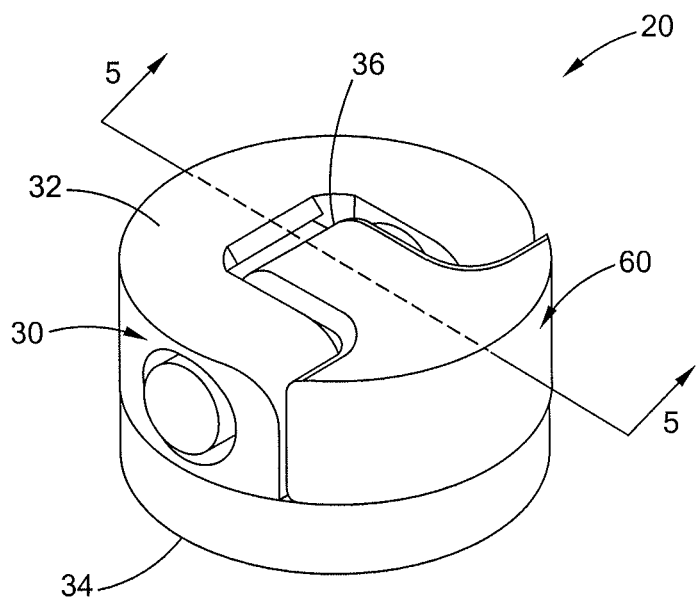
FIG. 1 is a plan view of an embodiment of a device for retaining a suture on a bodily wall.

Turning now to the figures, FIGS. 1-7 depict an embodiment of a device 20 for retaining a suture 100 (FIG. 5) on a bodily wall, such as in gastropexy. As seen in FIG. 1, the device 20 generally comprises a base member 30 and swivel member 60. As will be described further herein below, the swivel member 60 is rotatably attached to the base member 30 for rotation between open and closed configurations to fix the suture 100. Generally, the device 20 and the base member 30 include an upper surface 32 and a lower surface 34. The lower surface 34 is intended to rest against the bodily wall (such as the abdomen) while a suture 100 (which is typically fixed to another bodily wall or structure such as the stomach wall using an anchor) passes through a bore 36 from the lower surface 34 to the upper surface 32 where it can be manipulated by the operator such as a medical professional.

Figure 2:
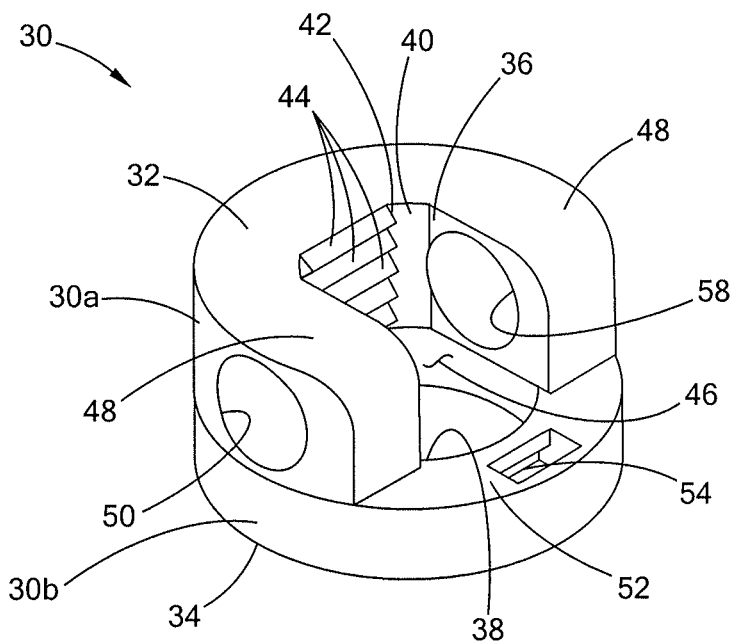
FIG. 2 is a plan view of a base member forming part of the device of FIG. 1.

As best seen in FIG. 2, the base member 30 generally comprises an upper base portion 30a and lower base portion 30b. The upper base member portion 30a is generally C-shaped or U-shaped, while the lower base member portion 30b is generally ringed-shaped (e.g. annular). The upper and lower base member portions 30a, 30b may be integrally and unitarily formed such as in a molding process, or alternatively they may be separately formed and attached together by adhesives, welding or bonding techniques known to the skilled artisan. Preferably the device 30 is formed of a plastic material suitable for being maintained against a bodily wall of a mammalian patient, such as polytetrafluorethylene (PTFE), expanded polytetrafluorethylene (EPTFE), polyethylene ether keytone (PEEK), polyvinylchloride (PVC), polycarbonate (PC), polyamide including Nylon(™), polyimide, polyurethane, polyethylene (high, medium or low density), and elastomers such as Santoprene (™), although suitable ceramics or metals or combinations of any of the foregoing may be employed.

The bore 36 extending through the base member 30 defines a bore surface, which as shown is formed by a lower bore surface 38 defined in the lower base member portion 30b, and an upper bore surface 40 defined by the upper base member portion 30a. The upper bore surface 40 defines a base jaw surface 42 which is formed by a plurality of elongated teeth 44 that generally have a triangular cross-section, and are arranged in a vertical series as shown in FIG. 2. The base member 30, and in particular the upper base member portion 30a, defines a recess 46 in communication with the bore 36, and which is sized to receive the swivel member 60. That is, the recess 46 leaves two flanges 48 in the upper base member portion 30a that help define the C-shape or U-shape. The flanges 48 define apertures 50 sized to receive pins 68 (FIG. 3) from the swivel member 60 for providing the pivotal attachment and rotation of the swivel member 60 relative to the base member 30.

It can also be seen in FIG. 2 that the recess 46 and the shape of the upper base member portion 30a leaves an upper surface 52 of the lower base member portion 30b exposed. In turn, this surface 52 defines an aperture 54 which has a general L-shape (best seen in FIG. 5) and which is used to form a portion of a lock to selectively fix the swivel member 60 to the base member 30.

Figure 3:
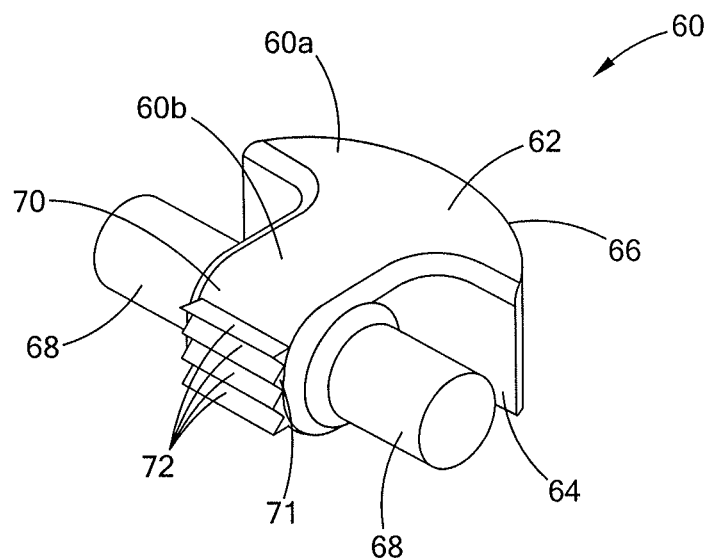
FIG. 3 is a plan view of swivel member forming a portion of the device of FIG. 1.

Turning now to FIG. 3, the swivel member 60 is generally T-shaped to correspond with the recess 46 in the base member 30. The T-shape is generally defined by a cross portion 60a and a stem portion 60b. The swivel member 60 generally has an upper surface 62, a lower surface 64, and a side surface 66. The upper surface 62 is designed to be flush with the upper surface 32 of the base member 30 when the device is in its closed configuration. Likewise, the side surface 66 is design to match the generally annular side surface of the base member 30, such that the device 20 has a general disc shape when the device 20 is in its closed position (see FIG. 1). As used herein, disc shape refers to a shape that is has a diameter or width that is larger than a thickness or height, such as a plate or other flat object. Although a round disc shape is shown, the device may have a polygonal disc shape such as square.

Figure 4:
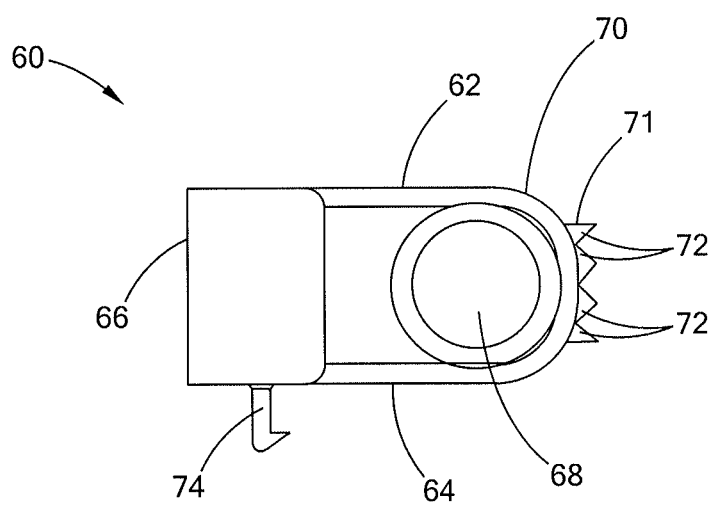
FIG. 4 is a side view of the swivel member shown in FIG. 3.

The stem portion 60b of the swivel member 60 includes two pins 68 projecting laterally therefrom, and which are sized and positioned to be placed through the apertures 50 in the base member 30. The pins 68 may be integrally and unitarily formed with the swivel member 60, or may be separately formed and attached. Still further, the pins 68 may be combined into a single pin which is placed through the apertures 50 and the base member 30 and a corresponding aperture in the stem 60b of the swivel member 60. In this case, the single pin can be attached to the stem 60b by friction fit or other mechanical connections such as adhesives, welding or bonding techniques. The stem portion 60b of the swivel member 60 generally includes an end surface 70 that is opposite the side surface 66 of the cross member 60a. The end surface 70 defines a swivel jaw surface 71 formed by a plurality of teeth 72 arranged linearly in series and corresponding to the teeth 44 of the base jaw surface 42. That is, the swivel jaw surface 70 and the base jaw surface 42 have teeth 72, 44 that are sized and structured to mesh in the closed position to fix the suture 100 to the device 20, as will be discussed herein with reference to FIGS. 5-7. As best seen in FIG. 4, the swivel member 60 also includes an L-shaped tab 72 projecting downwardly from the lower surface 64. The tab 72 is structured to selectively engage the L-shaped opening 54 in the base member 30, to selectively lock the swivel member 60 to the base member 30.

Figure 5:
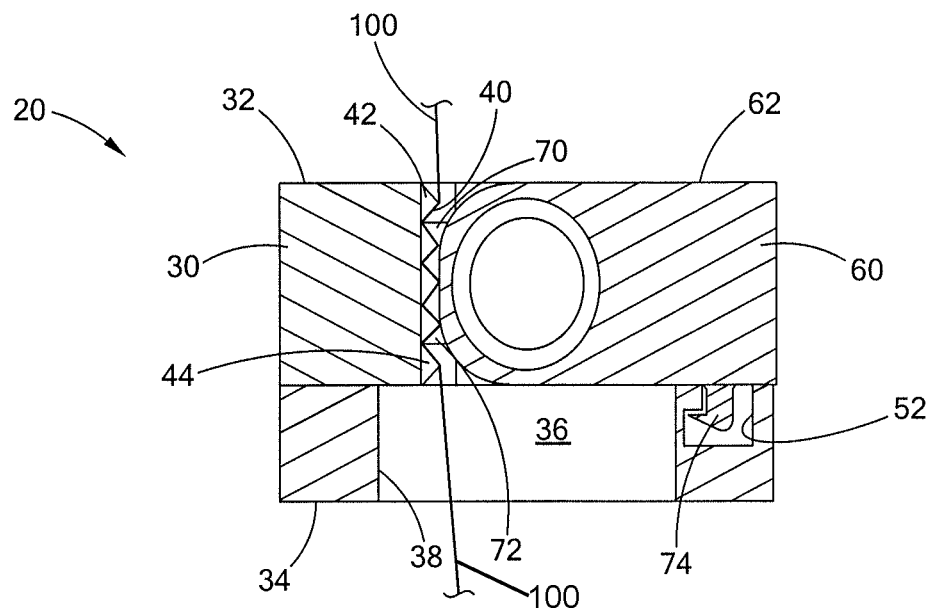
FIG. 5 is a cross-sectional view of the device of FIG. 1.

As best seen in FIG. 5, when the device 20 is in its closed configuration, the swivel member 60 is fit within the recess 46 of the base member 30 such that the upper surfaces 32, 62 are generally coplanar (as are the side surfaces which form an annular disc-shape) while the locking tab 74 of the swivel member 60 is engaged with the opening 52 in the base member 30 to maintain their relative positioning and fixation of the suture. Notably, the swivel jaw surface 71 and the base jaw surface 42 are sized and structured to mesh in this closed position such that the series of teeth 44, 72 (having inter-meshed triangular cross-sections) form a tortuous pathway that frictionally engages and fixes the suture 100 that passes through the bore 36 of the device 20.

Figure 6:
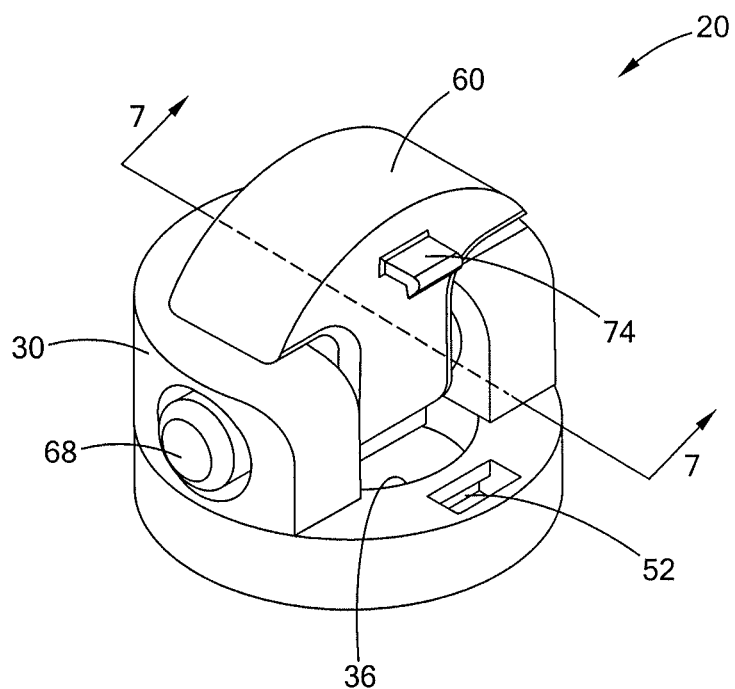
FIG. 6 is a plan view of the device of FIG. 1 shown in an open configuration.
Figure 7:
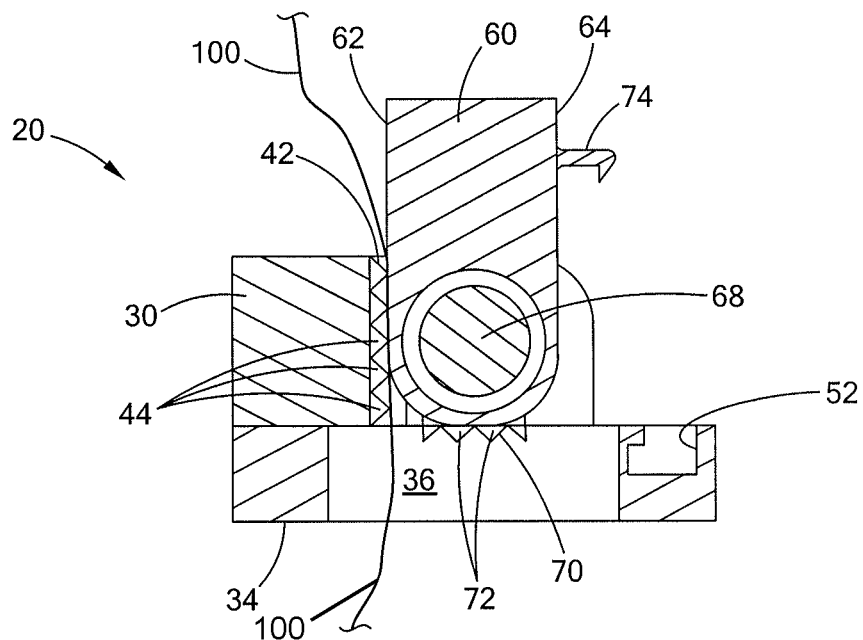
FIG. 7 is a cross-sectional view of the device as shown in FIG. 6.

The locking tab 74 is preferably formed of a plastic material and has a size and structure that permits elastic deformation of the tab 74 such that it can move radially (to the right on the page in FIG. 5) for withdrawal from the aperture 52 to move the swivel member 60 to an open configuration, as shown in FIGS. 6 and 7. As seen in the figures, the relative sizing of the upper base member portion 30a (i.e. thickness) the pins 68 and corresponding apertures 50 and the relative sizes of the stem portion 60b and cross-portion 60a of the swivel member 60 are such that the swivel member 60 can rotate through about 180 degrees to the position shown in FIGS. 6 and 7. In this open configuration, the suture 100 runs through the bore 36 and may be slid therethrough, such as for tensioning the body structures attached to the suture 100 below the lower surface 34 of the base member 30. The teeth 44 of the base jaw surface 42 may slightly engage the upper surface 62 of the swivel member 60, and any friction therebetween can be overcome through appropriate tensioning of the suture 100.

Notably, as swivel member 60 is rotated from the open configuration (FIGS. 6-7) towards the closed configuration (FIGS. 1, 5), i.e. as the swivel member 60 is rotated downwardly towards the right on the page in FIG. 7, the swivel jaw surface 71 rotates upwardly and to the left on the page such that the closing action of the device 20 serves to begin engaging the suture 100. This movement slightly increases the tension on the suture 100 in an upwardly direction, as the teeth 44, 72 begin to engage each other. In this way, when the lower end of the suture 100 is affixed to a bodily structure (such as the stomach wall) the closing action of the device 20 will serve to slightly increase tension already placed on the suture 100, thereby insuring a secure level of tension on the suture 100 and on the bodily walls (such as the stomach wall to the abdominal wall). The teeth 44 and/or teeth 72 are preferably constructed to be elastically deformable such that, as they are rotated into the closed configuration and along the opposing jaw surface 42, 71, they may slightly deflect while passing along the opposing teeth 44, 72. In the closed position shown in FIG. 5, the teeth 44, 72 are intermeshed and securely engage the suture 100 such that the suture 100 is fixed to the device and additional tension on either end of the suture 100 will not allow movement of the suture 100 relative to the device 20. To release the suture 100, the swivel member 60 may again be rotated from the closed position to the open position by sufficient force on the swivel member 60, which causes the tab 74 to deflect outwardly and become dislodged from the aperture 52 in the base member 30, as previously discussed.

Figure 8:
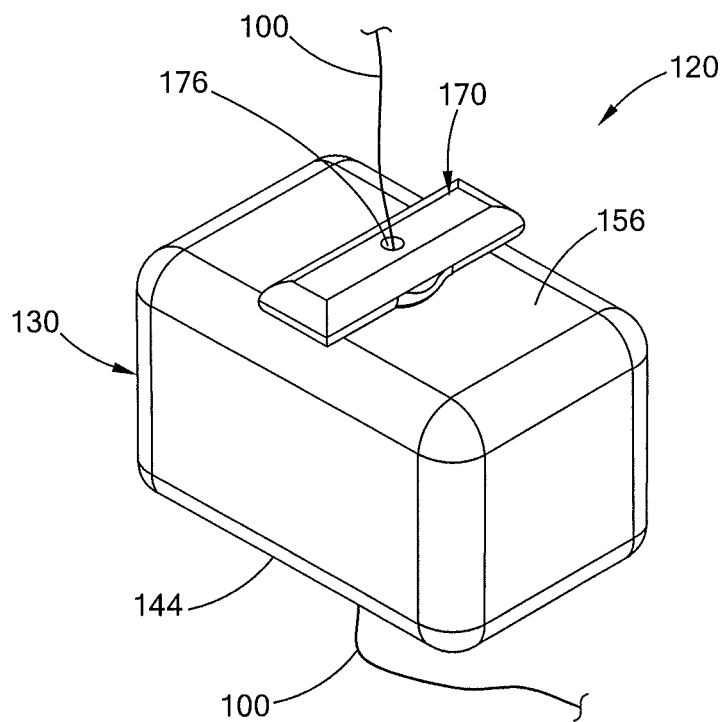
FIG. 8 is a plan view of another embodiment of a device for retaining a suture on a bodily wall.

Turning now to FIG. 8, another embodiment of the device 120 for retaining a suture 100 on a bodily wall is depicted. The device generally includes a base member 130 and a key 170 selectively attachable to the base member 130. The device includes an unlocked configuration where the key is attached to the base member (as shown in FIG. 8) to allow the suture to slide relative to the device 120. In a fully locked configuration (FIG. 16), the key 170 is detached from the base member 130 such that the suture 100 is fixed to the base member 130 as it extends therethrough from a bottom surface 144 to a top surface 156.

Figure 9:
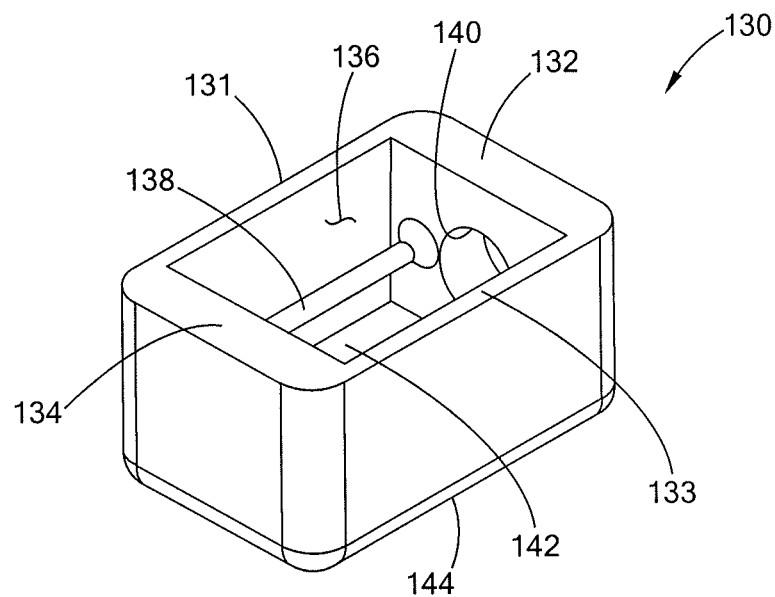
FIG. 9 is a plan view of a base member forming a portion of the device of FIG. 8.

As shown in FIG. 9, the base member 130 includes side walls 131, 132, 133, 134 arranged to form a box-like shape, i.e. square or rectangular, and defines an interior space 136. A bottom wall 142 is connected to the side walls 131, 132, 133, 134 to close off the bottom and define the lower surface 144 of the base member 130. These walls are preferably integrally and unitarily formed, although they may be separately formed and joined by adhesives, friction fit, welding, bonding or other mechanical connecting techniques known to those skilled in the art. One side wall, shown as wall 132 in FIG. 9, defines a pocket 140 for receiving a biasing member, as will be described in further detail below. One or more rods 138, two in the currently preferred embodiment, extend between opposing side walls 132, 134 to serve as rails or guiding members, as will also be discussed further below.

Figure 10:
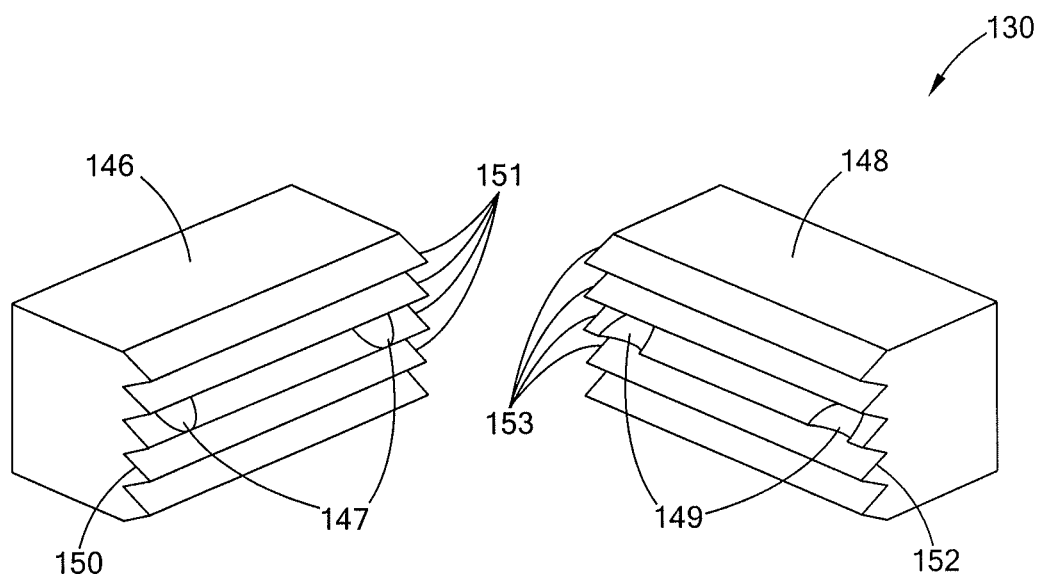
FIG. 10 is a plan view of jaw members forming a portion of the device of FIG. 8.

Turning to FIG. 10, the device 120 also includes a first jaw 146 and a second jaw 148 which are sized to fit within the interior space 136 of the base member 130. The first jaw 146 defines a first jaw surface 150 formed by a plurality of teeth 151, and likewise the second jaw 148 includes a second jaw surface 152 formed by a plurality of teeth 153. As with the prior embodiments, the teeth 151, 153 preferably have a triangular cross-section and are formed as a series of laterally extending and vertically spaced teeth for gripping the suture 100.

The first and second jaws 146, 148 include a pair of spaced apart passageways 147, 149 that are sized to slidably receive the rods 138 in the base member 130. In this way, the first and second jaws 146, 148 are translatable along the rods 138 for moving between open and closed positions corresponding to the above-mentioned unlocked and locked configurations. Alternatively, only one of the jaws 146, 148 needs to be slidable, and thus the other jaw may be formed unitarily and/or integrally with the base member 130 and corresponding side walls.

The rods 138 may be inserted through the jaws 146, 148 and then together inserted into space 136, or alternatively the jaws 146, 148 may be inserted into the space 136 and the rods 138 inserted through openings formed into the side walls that correspond to passageways 147, 149 of the jaws 146, 148. The rods 138 may be connected to the side walls by adhesives, friction fit, snap-fit, welding, bonding or other mechanical connection structures and techniques known to the skilled artisan.

Figure 11:
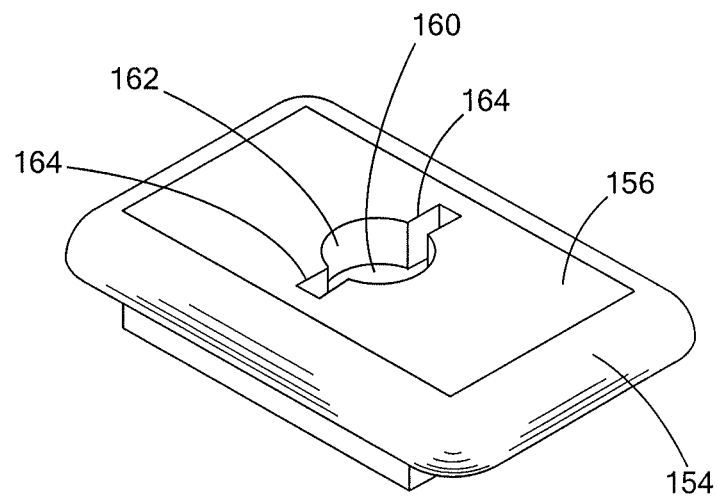
FIG. 11 is a plan view of top wall forming a portion of the base member depicted in FIG. 9.

The base member 130 also includes an upper wall 154 shown in FIG. 11. The upper wall 154 and the lower wall 142, together with the interior space 136, define a bore 160 extending through the base member 130 from the upper surface 156 to the lower surface 144. In particular, the upper wall 156 includes an upper hole 162 that is aligned with a lower hole 161 formed in the bottom wall 142 (see FIGS. 11, 13). The bore 160 permits the suture 100 to pass through the base member 130 by extending through the lower hole 161, the interior space 136, and the upper hole 162. The upper hole 162 is also designed to serve as a key hole to permit operation of the device 120 between its locked and unlocked configurations. In particular, the upper aperture 162 is asymmetrical, and in the embodiment shown in FIG. 11 includes two opposing wings 164 which extend away from a central axis of the upper hole 162. The upper wall 154 may be connected to the side walls by adhesives, friction fit, welding, bonding or other mechanical connection structures and techniques known to the skilled artisan.

Figure 12:
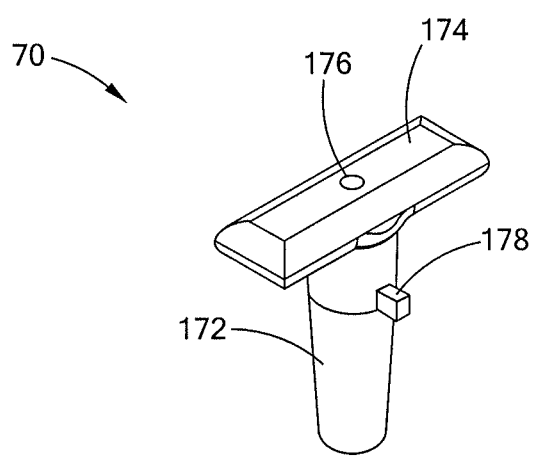
FIG. 12 is a plan view of a key forming a portion of the device of FIG. 8.

The key 170 is best seen in FIG. 12. The key 170 generally includes a key body 172 and a handle 174 fixedly attached to the key body 172 for manipulation by the operator. The key body 172 and handle 174 define a passageway 176 extending vertically through the key 170. The key 170, and in particular the key body 172, is sized and shaped to extend through the interior space 136 and hold the first and second jaw members 146, 148 in a spaced apart, unlocked, configuration. The passageway 176 through the key 170 is aligned with the lower hole 161 in the bottom wall 142, such that the suture 100 can pass through the entire device 120, namely from the bottom surface 144, through the lower hole 161 and through the passageway 176 in the key 170 to a position above the top surface 156 of the base member 130. The key body 172 also includes a pair of locking tabs 178 projecting outwardly therefrom. It can also be seen that the locking tabs 178 of the key 170 are sized to be passed through wings 164 of the upper hole 162 and rotated such that upward movement of the key 170 is blocked by the upper wall 154 (i.e. when the tabs 178 are not aligned with the wings 164 of hole 162).

Figure 13:
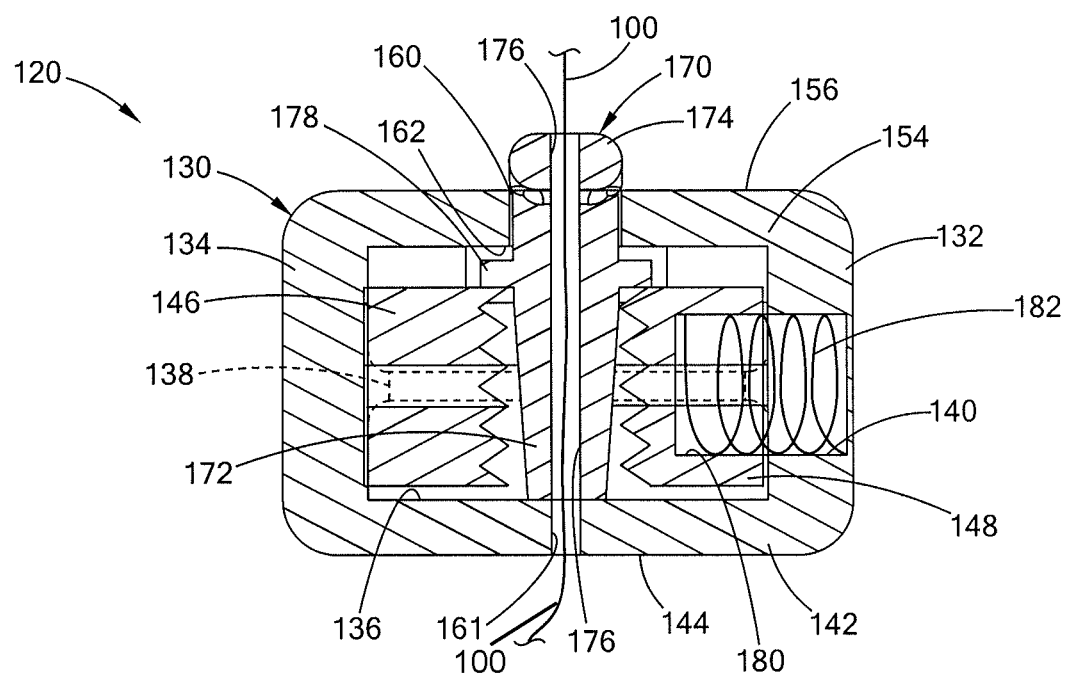
FIG. 13 is a cross-sectional view of the device depicted in FIG. 8.

Turning now to FIG. 13, the unlocked configuration of the device is shown. It can be seen that the base member 130 has been shown assembled with the side walls 131, 132, 133, 134 enclosed by the lower wall 142 and the upper wall 154. The first and second jaws 146, 148 are fitted within the interior space 136 of the base member 130, and slidably attached thereto via the rods 138. The second jaw 148 is biased towards the first jaw 146. In the depicted embodiment, the second jaw 148 includes a pocket 180 aligned with the pocket 140 formed in the side wall 132. A spring 182 is fitted within the pockets 140, 180 in order to bias the second jaw 148 towards the first jaw 146. In the unlocked configuration, the key 170 is attached to the base member 130 such that it extends through the bore 160, and in particular the upper hole 162 in upper wall 154, through the interior space 136, and is sized to rest against the bottom wall 142. The suture 100 passes through the passageway 176 in the key 170, as well as through the bore 160 in the base member 130.

Figure 14:
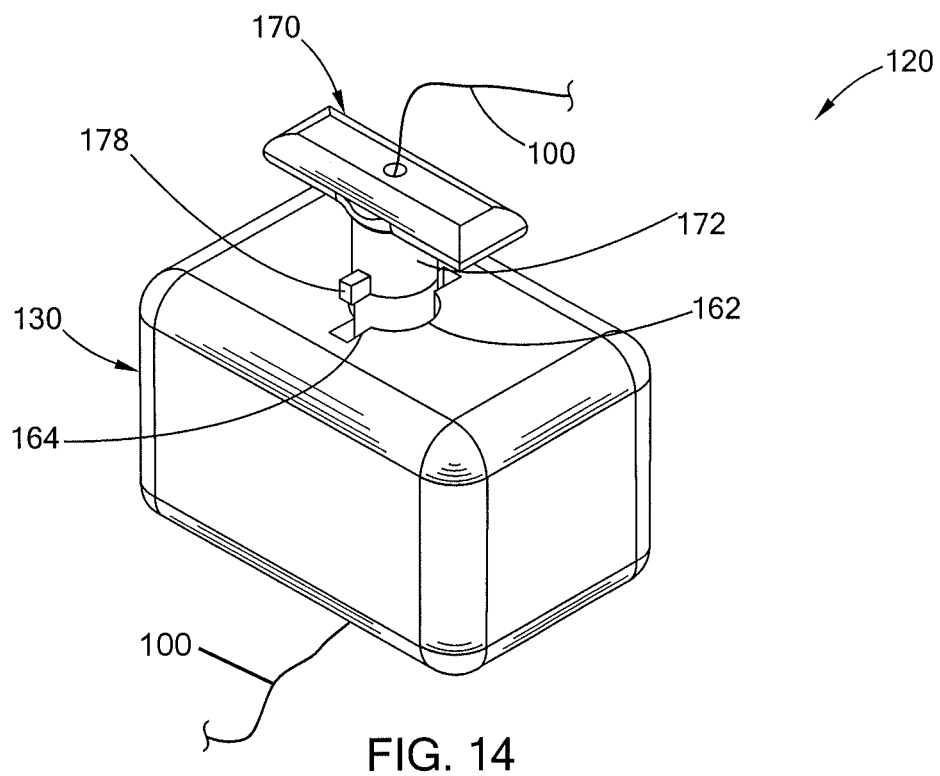
FIG. 14 is a plan view of the device of FIG. 8 shown in a partially closed configuration.
Figure 15:
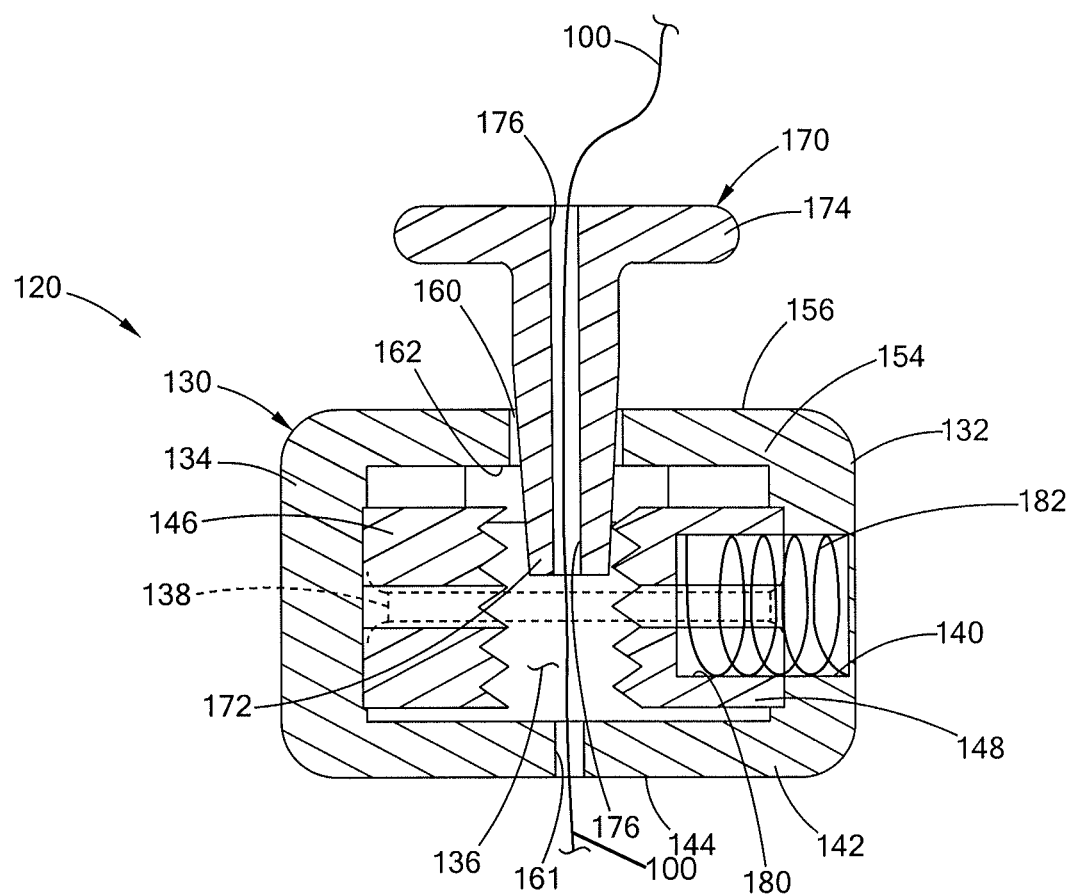
FIG. 15 is a cross-sectional view of the device shown in FIG. 14.
Figure 16:
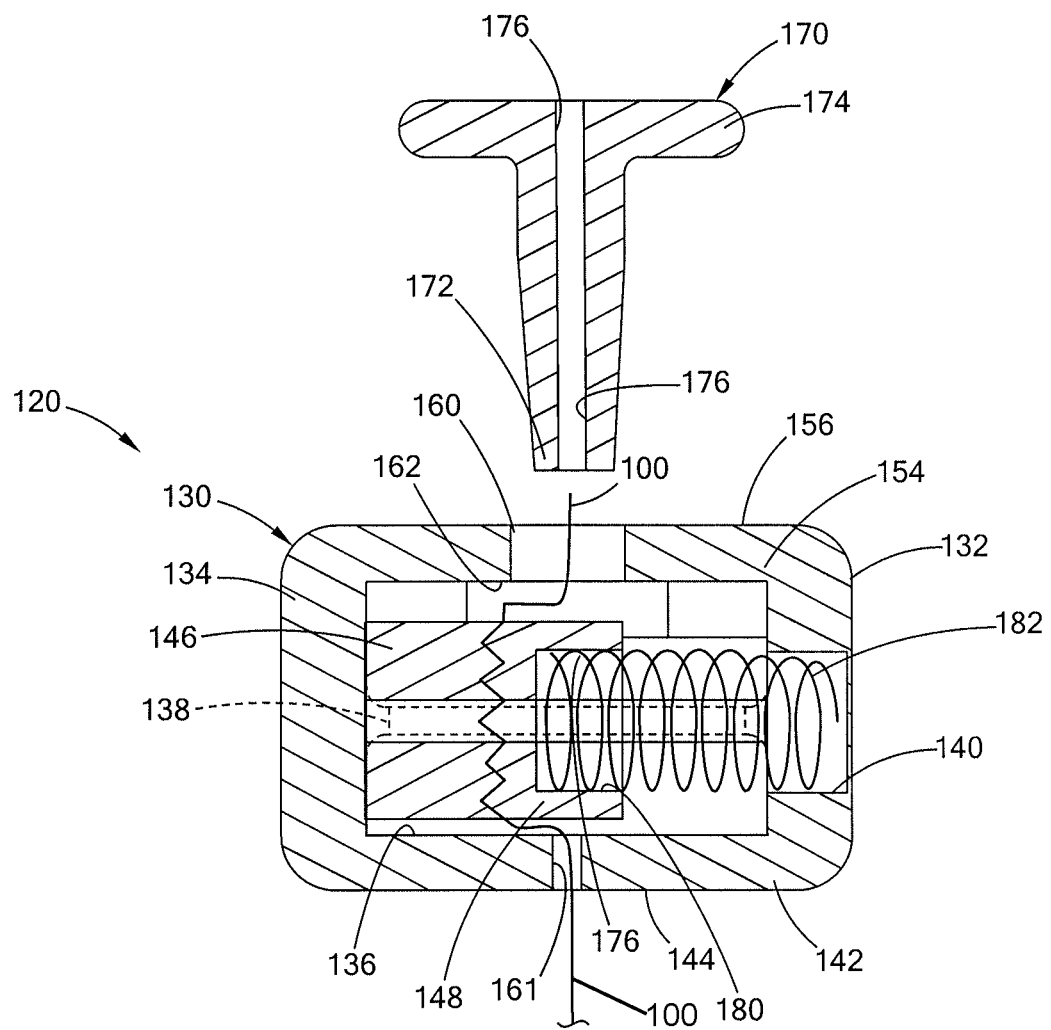
FIG. 16 is a cross-sectional view of the device of FIG. 8 showing a closed configuration.

As shown in FIGS. 14 and 15, once the suture 100 has been fed through the device 120 they are positioned at the desired location with the desired tension on the suture 100, the key 170 can be removed from the base member 130 to begin transitioning the device 120 from the unlocked configuration to the locked configuration. Generally, the key 170 is rotated by the operator by grasping the handle 174 and rotating it such that the locking tabs 178 are aligned with the wings 164 of the upper hole 164. The key 170 then may be vertically lifted (i.e. moved away from the bottom wall 142). The lower portion of the key body 172 is slightly tapered as shown, and thus the spring bias on second jaw 148 will also help to force the key 170 upwardly. When the key 170 is fully removed as shown in FIG. 16, the spring 182 will force the second jaw 148 to slide fully against the first jaw 146.

The first and second jaw surfaces 150, 152 will engage to define a tortuous pathway that is laterally offset from the bore 160, and namely laterally offset from the upper hole 162 and the lower hole 161. The key 170 may continue to be slid upwardly along the suture 170 until the suture 170 completely passes through the passageway 176 formed in the key 170. The suture 100 may then be cut such that it is positioned adjacent the upper surface 156 of the base member 130, as shown in FIG. 16. Trimming the suture 100 may be desirable before and/or after removing the key 170.

The foregoing description of various embodiments of the invention has been presented for purposes of illustration and description. It is not intended to be exhaustive or to limit the invention to the precise embodiments disclosed. The drawings are generally to scale and proportional, and the relative sizes and dimensions of the depicted structures are expressly included herein. Numerous modifications or variations are possible in light of the above teachings, and it will be recognized by the skilled practitioner that certain features of the described embodiments may be applied to other embodiments of the invention. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A device for retaining a suture on a bodily wall, the device comprising:
    a base member having an upper surface, a lower surface, and a bore extending from the upper surface to the lower surface and defining a bore surface, the bore surface including a base jaw surface; and
    a swivel member rotatably attached to the base member for rotation between an open position and a closed position relative to the base member, the swivel member including a swivel jaw surface in communication with the bore, the swivel jaw surface engaged with the base jaw surface in the closed position such that a suture passing through the bore and between the base jaw surface and the swivel iaw surface is fixed to the device by the base jaw surface and the swivel jaw surface, the swivel jaw surface disengaged from the base jaw surface in the open position such that the suture is not fixed to the device.

2. The device of claim 1, wherein the base member defines a recess in communication with the bore, the recess receiving the swivel member.

3. The device of claim 2, wherein the recess in the base member receives the swivel member in the closed position such that the base member and swivel member together have a disc shape.

4. The device of claim 2, wherein the recess opens to the upper surface of the base member.

5. The device of claim 4, wherein the base member includes a side surface extending from the upper surface to the lower surface, and wherein the recess in the base member also opens to the side surface.

6. The device of claim 2, wherein the recess defines two flanges in an upper portion of the base member, the upper portion having a C-shape.

7. The device of claim 6, wherein the swivel member is pivotally attached to the flanges of the base member.

8. The device of claim 1, further comprising a lock selectively fixing the swivel member to the base member.

9. The device of claim 8, wherein the lock includes a flexible tab formed on the swivel member and a corresponding aperture formed in the base member.

10. The device of claim 1, wherein the swivel jaw surface and the base jaw surface each include a series of teeth that are sized and structured to mesh in the closed position to fix the suture to the device.

11. The device of claim 10, wherein the bore defines an axis, and wherein the series of teeth on the base jaw surface are elongated in a direction generally transverse to the axis.

12. The device of claim 11, wherein the series of teeth are arranged in a vertical series.

13. The device of claim 1, wherein the swivel jaw surface moves towards the upper surface as the swivel jaw moves from the open position to the closed position.

14. The device of claim 13, wherein the swivel jaw surface selectively engages the based jaw surface as the swivel jaw approaches the closed position to draw the suture towards the upper surface.

15. The device of claim 1, wherein the swivel jaw surface and the base jaw surface frictionally engage the suture therebetween to fix the suture to the device.

16. The device of claim 1, wherein in the base jaw surface extends in a flat plane.

17. The device of claim 10, wherein movement of the swivel member from the open position to the closed position causes the series of teeth to engage the suture to increase the tension on the suture in an upwardly direction.

18. The device of claim 10, wherein the series of teeth are constructed to be elastically deformable such that, as the swivel member is rotated into the closed configuration, opposing teeth in the series of teeth deflect against each other.

19. The device of claim 1, wherein the swivel jaw surface is directly engaged with the base jaw surface in the closed position.

20. A device for retaining a suture on a bodily wall, the device comprising:
 a base member having an upper surface, a lower surface, and a bore extending from the upper surface to the lower surface and defining a bore surface, the bore surface including a base jaw surface; and
 a swivel member rotatably attached to the base member for rotation between an open position and a closed position relative to the base member, the swivel member including a swivel jaw surface in communication with the bore, the swivel jaw surface engaged with the base jaw surface in the closed position such that a suture passing through the bore is fixed to the device by the base jaw surface and the swivel jaw surface, the swivel jaw surface disengaged from the base jaw surface in the open position such that the suture is not fixed to the device;
 wherein the base member defines a recess in communication with the bore, the recess receiving the swivel member, wherein the recess defines two flanges in an upper portion of the base member, the upper portion having a C-shape, wherein the swivel member is generally T-shaped when viewed from above in the closed position and sized to mate with the C-shape of the upper portion of the base member.

* * * * *

UNITED STATES PATENT AND TRADEMARK OFFICE
CERTIFICATE OF CORRECTION

PATENT NO. : 10,631,846 B2  
APPLICATION NO. : 15/392239  
DATED : April 28, 2020  
INVENTOR(S) : Kristyn Gadlage et al.

It is certified that error appears in the above-identified patent and that said Letters Patent is hereby corrected as shown below:

In the Claims

In Column 8, Claim 1, Line 45, delete "iaw" and insert in its place --jaw--.

Signed and Sealed this  
Thirtieth Day of June, 2020

Andrei Iancu  
*Director of the United States Patent and Trademark Office*